(12) United States Patent
Sato (10) Patent No.: US 9,775,619 B2
(45) Date of Patent: Oct. 3, 2017

(54) COMPRESSION AND DECOMPRESSION CONTROL SYSTEM AND VASCULAR STRENGTHENING METHOD

(71) Applicant: KAATSU JAPAN Co, Ltd., Tokyo (JP)

(72) Inventor: Yoshiaki Sato, Tokyo (JP)

(73) Assignee: KAATSU JAPAN CO., LTD., Tokyo (JP)

( * ) Notice: Subject to any disclaimer, the term of this patent is extended or adjusted under 35 U.S.C. 154(b) by 317 days.

(21) Appl. No.: 14/408,702

(22) PCT Filed: Mar. 8, 2013

(86) PCT No.: PCT/JP2013/056522
§ 371 (c)(1),
(2) Date: Dec. 17, 2014

(87) PCT Pub. No.: WO2014/002531
PCT Pub. Date: Jan. 3, 2014

(65) Prior Publication Data
US 2015/0150560 A1    Jun. 4, 2015

(30) Foreign Application Priority Data

Jun. 28, 2012 (JP) .................................. 2012-145824
Sep. 28, 2012 (JP) .................................. 2012-215586

(51) Int. Cl.
*A63B 24/00* (2006.01)
*A61B 17/12* (2006.01)
(Continued)

(52) U.S. Cl.
CPC ........... *A61B 17/12* (2013.01); *A61H 9/0092* (2013.01); *A63B 21/0085* (2013.01);
(Continued)

(58) Field of Classification Search
CPC .................. A61B 17/12; A61H 9/0092; A61H 2201/1635; A61H 2201/164;
(Continued)

(56) References Cited

U.S. PATENT DOCUMENTS 5,738,612 A * 4/1998 Tsuda ................. A61B 5/02225
                                                              482/5
5,791,348 A   8/1998 Aung et al.
(Continued)

FOREIGN PATENT DOCUMENTS

CN    101351245 A    1/2009
EP      1949939 A1   7/2008
(Continued)

OTHER PUBLICATIONS

Heffernan et al., "External mechanical compression reduces regional arterial stiffness", Eur J Physiol (2007) 101: 735-741.
(Continued)

*Primary Examiner* — Glenn Richman
(74) *Attorney, Agent, or Firm* — Edell, Shapiro & Finnan, LLC (57) ABSTRACT

Provided are a method for strengthening blood vessels with extreme ease and a compression and decompression control system used for performing the method. A compression and decompression control system 1 includes a band adapted to be placed around a particular part of a limb of a user and to apply a compression force to the particular part and a controller for controlling the compression force applied to the particular part with the band. The controller controls the compression force applied with the band in a manner that a compression operation applying a predetermined compression force to the particular part and a decompression operation completely removing the compression force applied to the particular part by the compression operation are alter-
(Continued)

nately repeated. Repetition of the compression operation and the decompression operation allows the vascular endothelial cells of blood vessels of the user to generate a larger amount of nitric oxide, thereby strengthening the blood vessels.

32 Claims, 9 Drawing Sheets

(51) Int. Cl.
    *A63B 21/008*     (2006.01)
    *A63B 23/035*     (2006.01)
    *A63B 21/00*     (2006.01)
    *A61H 9/00*     (2006.01)
    *A63B 69/00*     (2006.01)

(52) U.S. Cl.
    CPC ...... *A63B 21/4025* (2015.10); *A63B 23/0355* (2013.01); *A63B 23/03508* (2013.01); *A63B 24/0087* (2013.01); *A63B 69/0059* (2013.01); *A61H 2201/164* (2013.01); *A61H 2201/165* (2013.01); *A61H 2201/1635* (2013.01); *A61H 2201/5002* (2013.01); *A61H 2201/5035* (2013.01); *A61H 2201/5071* (2013.01); *A63B 21/4011* (2015.10); *A63B 21/4017* (2015.10); *A63B 2208/053* (2013.01); *A63B 2209/10* (2013.01); *A63B 2213/006* (2013.01)

(58) Field of Classification Search
    CPC ...... A61H 2201/165; A61H 2201/5002; A61H 2201/5035; A61H 2201/5071
    See application file for complete search history.

(56) References Cited

U.S. PATENT DOCUMENTS

| | | | |
|---|---|---|---|
| 6,190,325 B1 * | 2/2001 | Narimatsu | A61B 5/0225 600/485 |
| 6,196,974 B1 * | 3/2001 | Miwa | A61B 5/02125 600/485 |
| 6,616,579 B1 * | 9/2003 | Reinbold | A63B 21/0023 482/1 |
| 7,448,984 B2 * | 11/2008 | Chow | A61H 9/0078 482/1 |
| 7,810,359 B2 * | 10/2010 | Hannula | A41D 20/00 2/181 |
| 8,328,693 B2 * | 12/2012 | Sato | A63B 21/00196 482/1 |
| 2003/0139255 A1 * | 7/2003 | Lina | A61F 13/065 482/24 |
| 2009/0221406 A1 | 9/2009 | Sato | |
| 2012/0083712 A1 | 4/2012 | Watson et al. | |

FOREIGN PATENT DOCUMENTS

| | | |
|---|---|---|
| EP | 2436308 A1 | 4/2012 |
| JP | 2670421 B2 | 10/1997 |
| JP | 2006110045 | 4/2006 |
| JP | 2008161418 | 7/2008 |
| JP | 4597840 B2 | 12/2010 |
| TW | 200727936 A | 1/2007 |

OTHER PUBLICATIONS

International Search Report, PCT/JP2013/056522, dated Apr. 2, 2013, 7 pages.
International Preliminary Report on Patentability and the Written Opinion, PCT/JP2013/056522, 10 pages, dated Dec. 31, 2014.

* cited by examiner

COMPRESSION AND DECOMPRESSION CONTROL SYSTEM AND VASCULAR STRENGTHENING METHOD

TECHNICAL FIELD

The present invention relates to a compression and decompression control system and a method for strengthening blood vessels.

BACKGROUND ART

A Kaatsu muscle training method capable of efficiently strengthening muscles by restricting a blood flow to apply a load to the muscles has been developed and is used in practice (for example, see Patent Document 1). In such a muscle training method, a muscle strengthening tool is used. The tool includes a tight fitting device with which a certain part of the limbs (arms and legs) of a user is tightened to apply a compression force to muscles. At the present time, a technique of increasing and decreasing the compression force applied to a certain part the limbs of a user is developed. The technique improves the efficiency of the Kaatsu muscle training and also improves the safety of the Kaatsu muscle training (for example, see Patent Document 2).

CITATION LIST

Patent Document(s)

Patent Document 1: JP2670421
Patent Document 2: JP4597840

SUMMARY OF THE INVENTION

Problem to be Solved by the Invention

Recent unhealthy lifestyles including irregular dietary habits and insufficient exercise result in an increase in the number of patients suffering from vascular diseases such as cerebral infarction and myocardial infarction. On this account, the studies aiming to strengthen blood vessels (improvement in vessel elasticity, for example) have been carried out in medical and other fields. The inventors of the present application have advanced the related art Kaatsu muscle training method as disclosed in Patent Documents 1 and 2 and have found a novel technique capable of strengthening blood vessels.

An object of the present invention is to provide a method for strengthening blood vessels with extreme ease and a compression and decompression control system used for carrying out the method.

Means for Solving the Problem

To achieve the object, a compression and decompression control system of the present invention includes a band adapted to be placed around a particular part of a limb of a user and to apply a compression force to the particular part, and a controller for controlling the compression force applied to the particular part with the band, the controller controlling the compression force applied with the band in a manner that a compression operation applying a predetermined compression force to the particular part and a decompression operation completely removing the compression force applied to the particular part by the compression operation are alternately repeated.

By adopting such a configuration, the compression force applied with the band can be controlled in a manner that a compression operation applying a predetermined compression force to a particular part of the limbs (arms and legs) of a user and a decompression operation completely removing the compression force applied to the particular part by the compression operation are alternately repeated. Such a system allows the vascular endothelial cells of blood vessels of the user to generate a larger amount of nitric oxide, thereby strengthening the blood vessels. In other words, by simply using a particular band and repeating compression and decompression of a particular part of a limb of a user, blood vessels of the user can be extremely easily strengthened.

The compression and decompression control system of the present invention may further includes a shape retaining member for retaining a loop shape of the band that has been placed around the particular part, a gas bag provided on the band, and a pressure control unit for supplying a gas to the gas bag through a certain tube or for removing a gas from the gas bag. In such a system, the controller can control the pressure control unit to achieve the compression operation and the decompression operation.

In the compression and decompression control system of the present invention, the controller may set a duration of each of the compression operation and the decompression operation within a range from 10 to 30 seconds.

In the compression and decompression control system of the present invention, the band may have a width ranging from 2.5 to 3 cm and be placed around a position near a base of an arm of the user, and the controller may set the compression force in the compression operation within a range from 100 to 300 mmHg and may set the number of times of each of the compression operation and the decompression operation to three to five times.

In the compression and decompression control system of the present invention, the band may have a width ranging from 5 to 6 cm and be placed around a position near a base of a leg of the user, and the controller may set the compression force in the compression operation within a range from 200 to 300 mmHg and may set the number of times of each of the compression operation and the decompression operation to five times.

In the compression and decompression control system of the present invention, for plural times of the compression operations, the controller may set the compression force in each compression operation to be higher than the corresponding compression force in the next preceding compression operation.

A method for strengthening blood vessels of the present invention includes alternately repeating a compression step of applying a compression force to a particular part of a limb of a user with a band that is adapted to be placed around the particular part and a decompression step of completely removing the compression force applied to the particular part in the compression step, thereby allowing vascular endothelial cells of blood vessels of the user to generate a larger amount of nitric oxide to strengthen the blood vessels.

If adopted, the method allows the vascular endothelial cells of blood vessels of the user to generate a larger amount of nitric oxide to strengthen the blood vessels by alternately repeating the compression step of applying a predetermined compression force to a particular part of the limbs (arms and legs) of a user with a band that is adapted to be placed around the particular part and the decompression step of completely removing the compression force applied to the particular part in the compression step. In other words, by simply using a particular band and repeating compression and decompression of a particular part of a limb of a user, blood vessels of the user can be extremely easily strengthened. The method for strengthening blood vessels is merely an invention relating to the strengthening of "blood vessels (blood vessels are also muscles)" (that is, an invention highly relating to "muscle training"), but includes no method for medical practice applied to patients by doctors or the like, and has industrial applicability.

In the method for strengthening blood vessels of the present invention, a shape retaining member for retaining a loop shape of the band that has been placed around the particular part, a gas bag provided on the band, and a pressure control unit for supplying a gas to the gas bag through a certain tube or for removing a gas from the gas bag may be used. In such a case, the pressure control unit may be controlled to perform the compression step and the decompression step.

In the method for strengthening blood vessels of the present invention, a duration of each of the compression step and the decompression step may be set within a range from 10 to 30 seconds.

In the compression step of the method for strengthening blood vessels of the present invention, the band may have a width ranging from 2.5 cm to 3 cm and be used to apply the compression force to a position near a base of an arm of the user, and the compression force may be set within a range from 100 to 300 mmHg. In such a case, the number of times of each of the compression step and the decompression step may be set to three to five times.

In the compression step of the method for strengthening blood vessels of the present invention, the band may have a width ranging from 5 cm to 6 cm and be used to apply the compression force to a position near a base of a leg of the user, and the compression force may be set within a range from 200 to 300 mmHg. In such a case, the number of times of each of the compression step and the decompression step may be set to five times.

In the method for strengthening blood vessels of the present invention, for plural times of the compression steps, the compression force in each compression step may be higher than the corresponding compression force in the next preceding compression step.

Effect of the Invention

The present invention can provide the method for strengthening blood vessels with extreme ease and the compression and decompression control system used for carrying out the method.

MODE FOR CARRYING OUT THE INVENTION

Embodiments of the present invention will be described with reference to drawings hereinbelow.

First, embodiments of the present invention will be described with reference to FIG. 1 to FIG. 7. In the present embodiment, a specific example of a compression and decompression control system 1 of the present invention and a method for strengthening blood vessels (hereinafter called "blood vessel training") carrying out by using the compression and decompression control system 1 will be described.

Figure 1:
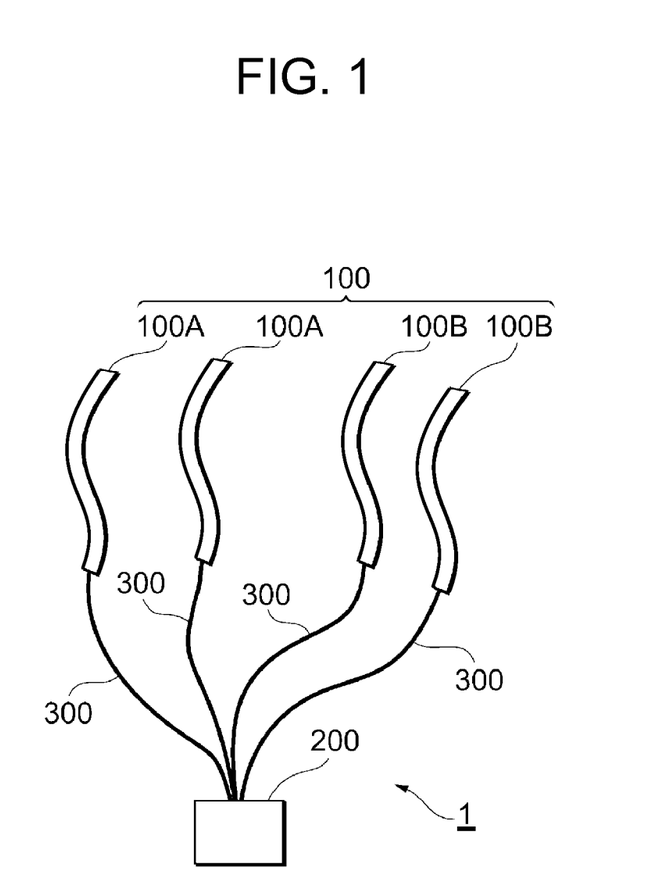
FIG. 1 is a schematic view illustrating an entire configuration of a compression and decompression control system pertaining to an embodiment of the present invention.

FIG. 1 is a schematic view illustrating the entire configuration of the compression and decompression control system 1 pertaining to the present embodiment. As shown in FIG. 1, the compression and decompression control system 1 pertaining to the present embodiment includes tight fitting devices 100 and a compression and decompression controller 200.

Figure 2:
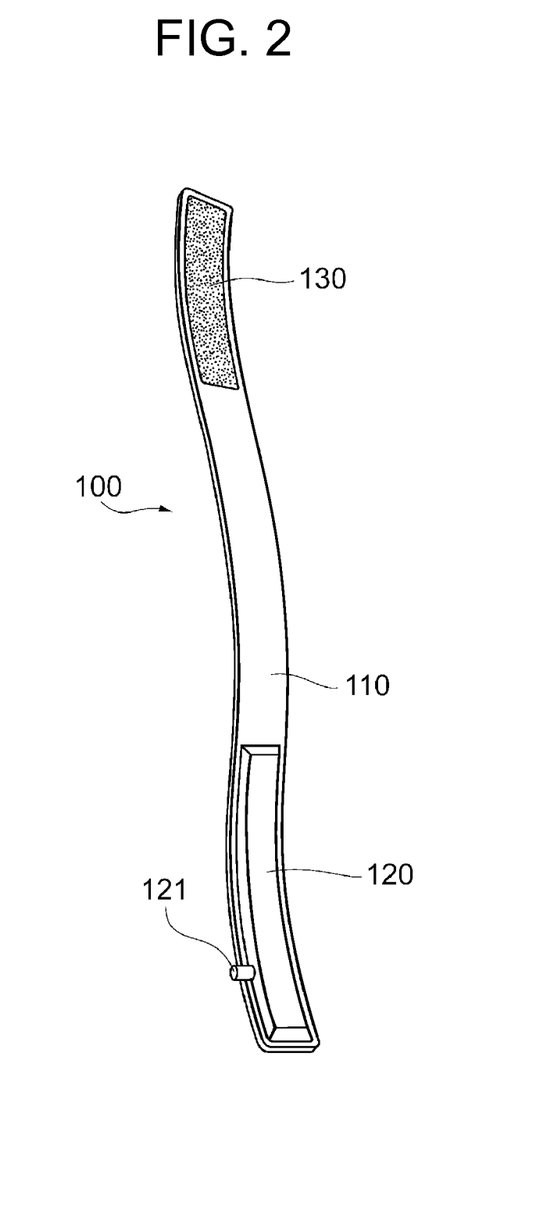
FIG. 2 is a perspective view illustrating a tight fitting device included in the compression and decompression control system illustrated in FIG. 1.
Figure 3:
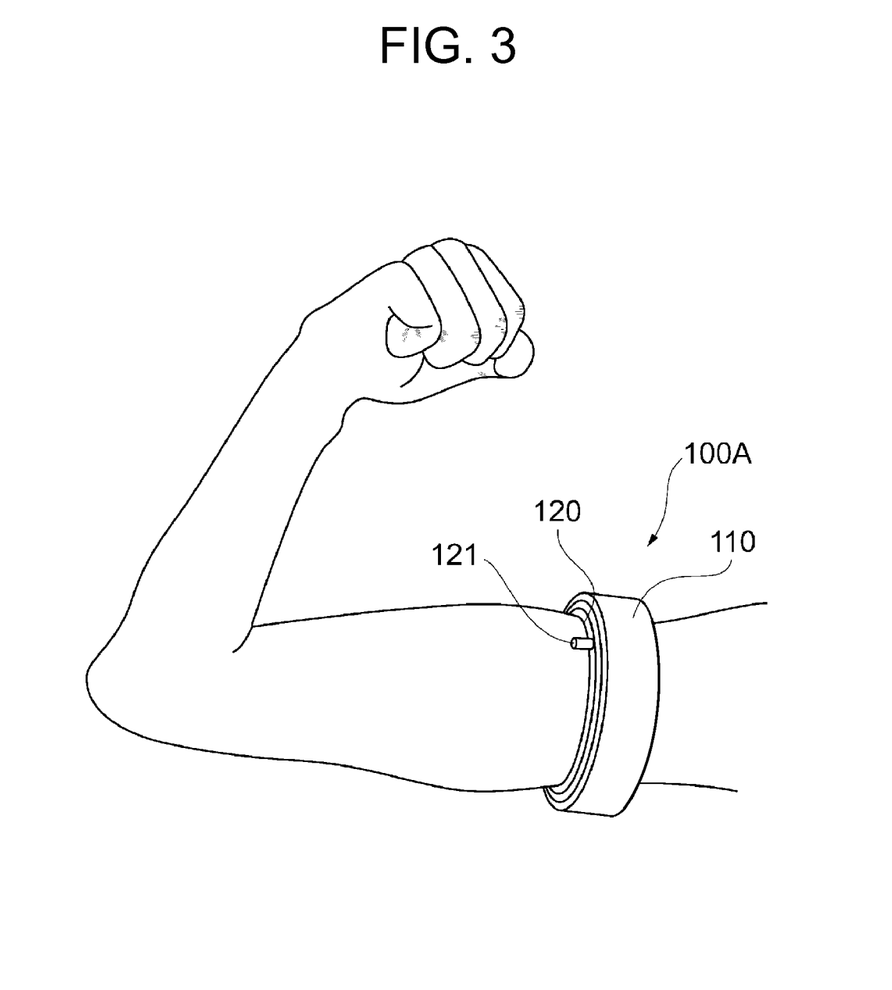
FIG. 3 is a view illustrating a use state of a tight fitting device for arms included in the compression and decompression control system illustrated in FIG. 1.
Figure 4:
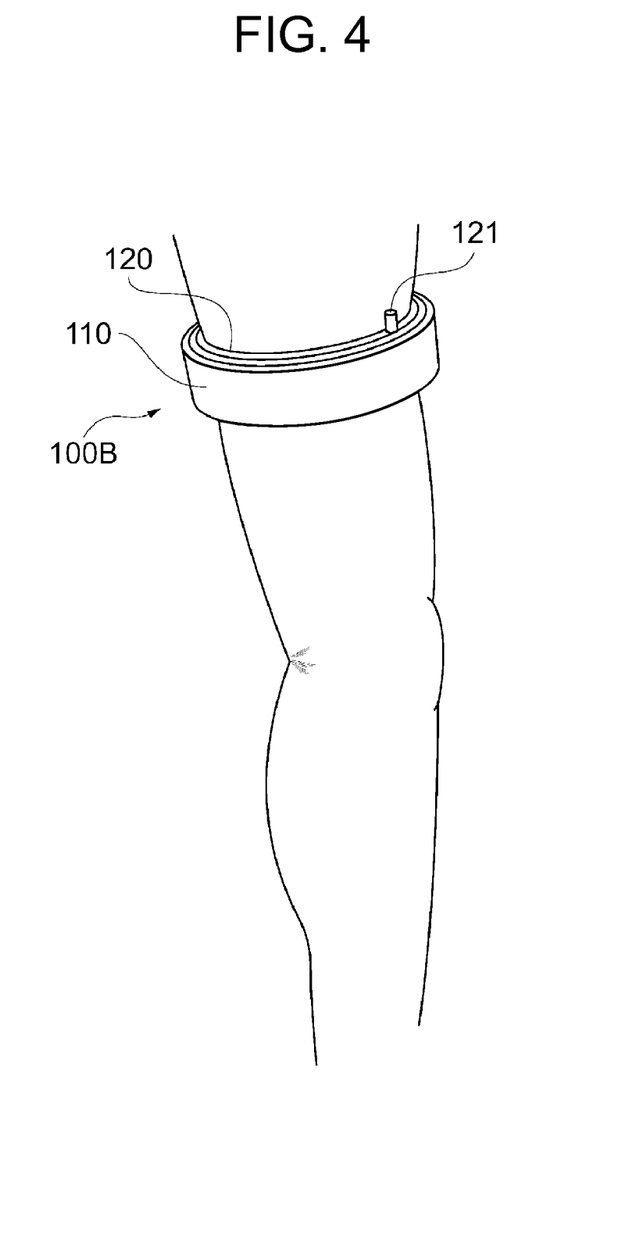
FIG. 4 is a view illustrating a use state of a tight fitting device for legs included in the compression and decompression control system illustrated in FIG. 1.

The tight fitting device 100 in the present embodiment is configured as shown in FIG. 2 to FIG. 4. FIG. 2 is a perspective view illustrating an embodiment of the tight fitting device 100, and FIG. 3 and FIG. 4 are perspective views illustrating usage patterns of the tight fitting devices 100.

The number of the tight fitting devices 100 in the present embodiment is plural (more specifically four) as shown in FIG. 1. The number of the tight fitting devices 100 is four so that a compression force can be applied to both arms and both legs of a user receiving the blood vessel training. Of the tight fitting devices 100 in the present embodiment, tight fitting devices 100A are used for arms (used to be placed around arms and to apply a compression force to the arms), and tight fitting devices 100B are used for legs (used to be placed around legs and to apply a compression force to the legs). The number of the tight fitting devices 100 is not necessarily four and may be one or more. The number of the tight fitting devices 100A for arms is not necessarily the same as that of the tight fitting devices 100B for legs. When the blood vessel training is subjected to a plurality of users, the number of the tight fitting devices 100 may be more than four.

The tight fitting device 100 in the present embodiment is adapted to be placed around a particular part of any muscles of the limbs and to tighten the particular part of the muscles to apply a predetermined compression force to the particular part, and can vary the compression force applied to the particular part of arms or legs as described later. In the present embodiment, the tight fitting device 100 basically includes a band 110, a gas bag 120, and a shape retaining member 130.

The band 110 may be any band that can be placed around a particular part (for example, a position near the base of an arm or the base of a leg and suitable for restricting the blood flow by tightening the position from the outside) around which the tight fitting device 100 is placed. The band 110 in the present embodiment is made of an elastic material, but not necessarily so. The band 110 is more specifically made of a neoprene rubber.

The length of the band 110 in the present embodiment can be set depending on a circumferential length of the particular part, around which the tight fitting device 100 is placed, of a user receiving the blood vessel training. The band 110 is required to have a length longer than the circumferential length of the particular part, and the band 110 in the present embodiment has a length longer than double the circumferential length of the particular part. The length of the band 110 of the tight fitting device 100A for arms in the present embodiment is specifically 90 cm in consideration that the particular part of an arm of a user receiving the blood vessel training has a circumferential length of 26 cm. The length of the band 110 of the tight fitting device 100B for legs is specifically 145 cm in consideration that the particular part of a leg of a user receiving the blood vessel training has a circumferential length of 45 cm.

The width of the band 110 in the present embodiment is appropriately set depending on a particular part around which the tight fitting device 100 is placed. For example, the width of the band 110 of the tight fitting device 100A for arms can be set within a range from 2.5 to 3 cm, and the width of the band 110 of the tight fitting device 100B for legs can be set from 5 to 6 cm.

The gas bag 120 is attached to the band 110. The gas bag 120 in the present embodiment is attached onto one side of the band 110. The gas bag 120 may be attached to the band 110 in any manner including the above. For example, the gas bag 120 may be provided inside a band 110 having a hollow inner space.

The gas bag 120 is, but not necessarily so, attached to the band 110 so that one end of the gas bag is aligned to one end of the band 110 (the lower end of the band 110 in FIG. 2). The gas bag 120 is an airtight bag made of an airtight material. The gas bag 120 in the present embodiment is made of a rubber having an elasticity similar to that of a rubber bag used for manchettes. The material of the gas bag 120 is not limited to the above, and any material capable of maintaining air tightness can be appropriately selected to satisfy the purpose.

The length of the gas bag 120 is substantially the same as the circumferential length of the particular part around which the tight fitting device 100 in the present embodiment is placed, but not necessarily so. In the present embodiment, the gas bag 120 of the tight fitting device 100A for arms has a length of 25 cm, and the gas bag 120 of the tight fitting device 100B for legs has a length of 44 cm.

The width of the gas bag 120 is appropriately set depending on a particular part around which the tight fitting device 100 is placed. In the present embodiment, the gas bag 120 of the tight fitting device 100A for arms has a width ranging from 2.5 to 3 cm, and the gas bag 120 of the tight fitting device 100B for legs has a width ranging from 5 to 6 cm, but not necessarily so.

The gas bag 120 has a connection port 121 communicating with the inside of the gas bag 120. For example, the connection port can connect to the compression and decompression controller 200 via a connection tube 300 composed of an appropriate tube such as a rubber tube. As described later, a gas (air in the present embodiment) is supplied into the gas bag 120 via the connection port 121, and the gas in the gas bag 120 is removed to the exterior via the connection port 121.

The shape retaining member 130 is used for fastening the band 110 so as to maintain the band 110 placed around the particular part. The shape retaining member 130 in the present embodiment is a hook and loop fastener provided on the band 110 at the other end of the side on which the gas bag 120 is provided (the upper end of the band 110 in FIG. 2). The shape retaining member 130 can be detachably fastened onto any area in the entire surface of the band 110 opposite to the gas bag 120.

When the band 110 is placed around a particular part, then the band 110 is fastened by the shape retaining member 130, and air is supplied to the gas bag 120, the tight fitting device 100 tightens muscles and applies a compression force to the muscles. When the air in the gas bag 120 is removed under such a circumstance, the tight fitting device 100 applies a lower compression force to the muscles.

The compression and decompression controller 200 may be any device capable of supplying a gas to the gas bag 120 and capable of removing the gas from the gas bag 120. The compression and decompression controller 200 also automatically controls the supply of a gas to the gas bag 120 and the removal of the gas. The compression and decompression controller 200 may have any configuration capable of supplying a gas to the gas bag 120 and removing the gas from the gas bag 120 and capable of performing the automatic control.

Figure 5:
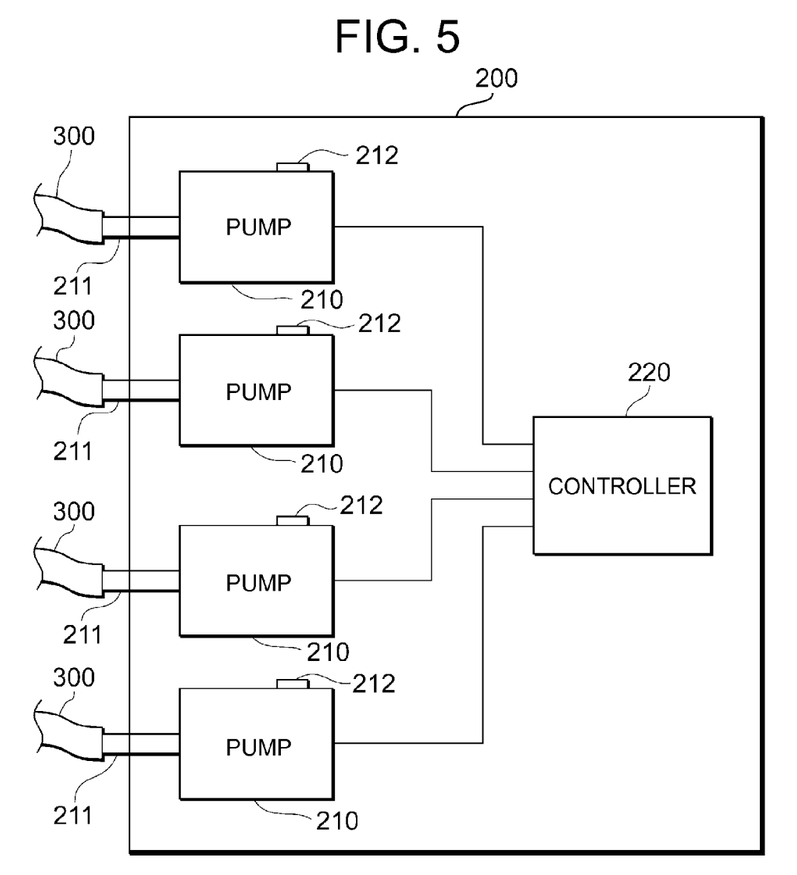
FIG. 5 is a schematic view illustrating an internal configuration of a compression and decompression controller included in the compression and decompression control system illustrated in FIG. 1.

FIG. 5 is a schematic view illustrating an exemplary configuration of the compression and decompression controller 200. As shown in FIG. 5, the compression and decompression controller 200 includes four pumps 210 and a controller 220. In the present embodiment, the compression and decompression controller 200 includes a housing, in which the pumps 210 and the controller 220 are placed. An input device is provided outside the housing but is not shown in drawings.

The four pumps 210 are associated with respective four tight fitting devices 100. In the present embodiment, the pump 210 corresponds to the pressure control unit in the present invention.

The pump 210 has a function to suck a gas (air in the present embodiment) present around the pump and to supply the gas to the outside via a pump connection port 211. The pump 210 also has a valve 212, through which the gas in the pump 210 can be discharged to the outside by opening the valve 212. Each of the four pumps 210 has the corresponding pump connection port 211 and is connected to the gas bag 120 via the connection tube 300 connected to the pump connection port 211 and via the connection port 121. When the pump 210 sends a gas, the gas is supplied into the gas bag 120. When the pump 210 opens the valve 212, the gas can be removed from the gas bag 120. The valve 212 is not necessarily provided on the pump 210, and may be provided at any position on the route from the pump 210 to the gas bag 120.

The pump 210 has a pressure gauge, which is not shown in drawings. With the pressure gauge, the pressure in the pump 210 can be measured. The pressure in the pump 210 is naturally equal to the pressure in the gas bag 120.

The controller 220 controls the pumps 210. The controller 220 controls the supply of air into the gas bag 120 of the tight fitting device 100 by driving the pump 210 with the valve 212 closed and the removal of the air in the gas bag 120 by opening the valve 212 on the pump 210. In other words, the controller 220 controls the driving of the pump 210 including the opening and closing of the valve 212.

The controller 220 controls the pump 210 so as to alternately repeat a compression operation that applies a predetermined compression force to the particular part with the band 110 of the tight fitting device 100 and a decompression operation that completely removes the compression force applied to the particular part by the compression operation. Repetition of such a compression operation and a decompression operation allows the vascular endothelial cells of blood vessels of a user to generate a larger amount of nitric oxide, thereby strengthening the blood vessels.

Figure 6:
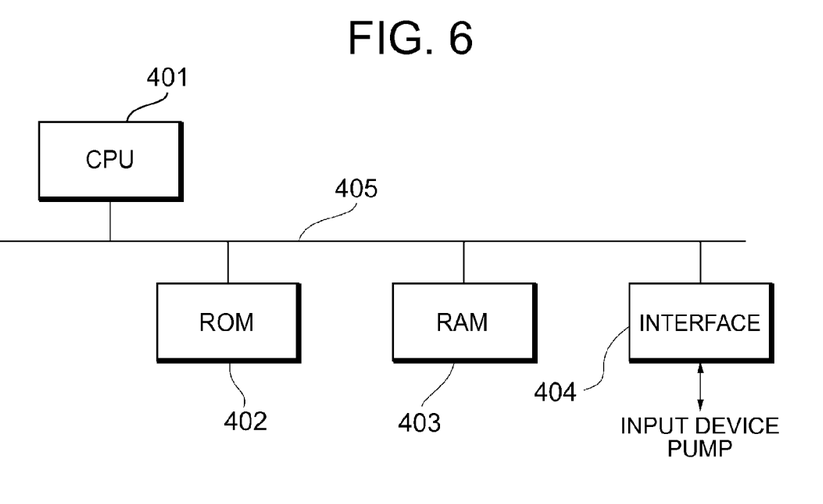
FIG. 6 is a view illustrating a hardware configuration of the controller included in the compression and decompression controller illustrated in FIG. 5.

The internal configuration of the controller 220 is schematically shown in FIG. 6. The controller 220 includes a computer and is composed of a CPU 401, a ROM 402, a RAM 403, and an interface 404, which are connected via a bus 405.

The CPU 401 is a central processing unit and controls the entire controller 220. The ROM 402 stores programs and data required for the processing described later executed in the controller 220, and the CPU 401 executes the processing on the basis of the program. The ROM 402 may be composed of a flash ROM. In addition to the ROM 402 or together with the ROM 402, the controller 220 may include other recording media for storing the programs and data, such as hard disks. The RAM 403 provides a work area for executing the program. The interface 404 has functions of receiving an input from an input device and sending instructions from the controller 220 to the respective four pumps 210.

Figure 7:
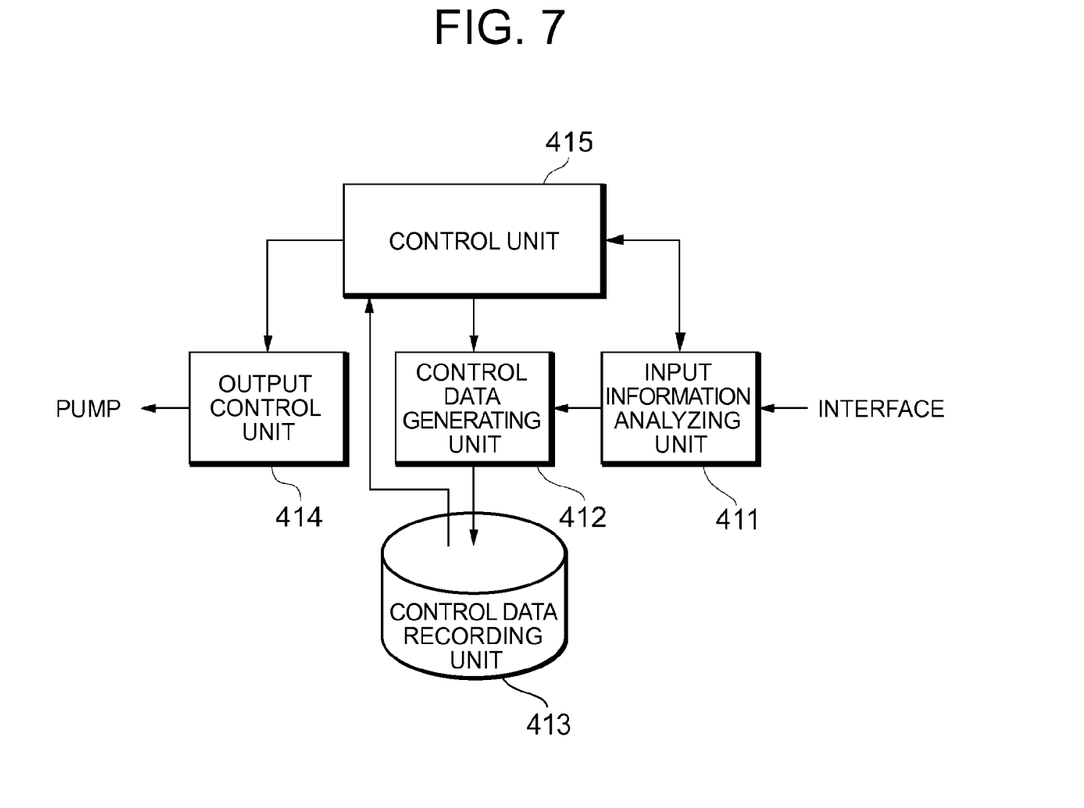
FIG. 7 is a view illustrating a functional block created in the controller included in the compression and decompression controller illustrated in FIG. 5.

When the CPU 401 executes the program, the functional block as shown in FIG. 7 is created in the controller 220. The controller 220 includes an input information analyzing unit 411, a control data generating unit 412, a control data recording unit 413, an output control unit 414, and a control unit 415.

The input information analyzing unit 411 receives an input from the input device through the interface 404 and analyzes the details of the input. The data analyzed by the information analyzing unit 411 is sent to the control data generating unit 412 or the control unit 415.

The control data generating unit 412 generates control data for controlling the pumps 210 including the opening and closing of the valves 212 on the basis of the data received from the input information analyzing unit 411. The control data generating unit 412 records the generated control data in the control data recording unit 413.

The control data recording unit 413 stores the control data received from the control data generating unit 412. The control data recording unit 413 in the present embodiment stores the respective pieces of control data associated with the four pumps 210 as a set. The control data recording unit 413 in the present embodiment can store plural sets of the respective pieces of control data associated with the four pumps 210. Each set of the pieces of data is the data set for controlling the compression forces to both arms and both legs when the blood vessel training is performed. The plural sets of the pieces of data may be the data sets for a plurality of users. In this case, depending on a user receiving the blood vessel training, the data set for the user receiving the blood vessel training is loaded. The plural sets of the pieces of data may be the data sets for a particular single user receiving the blood vessel training. In this case, a different data set can be loaded depending on physical conditions of the single user. Alternatively, the plural sets of the pieces of data can be used in both the above using manners The control unit 415 controls all the input information analyzing unit 411, the control data generating unit 412, the output control unit 414 as a whole. The control unit 415 also as a function of controlling the modes described later. The control unit 415 further has a function of reading a control data set from the control data recording unit 413 and sending the data set to the output control unit 414 when the blood vessel training is performed.

The output control unit 414 has a function of controlling the pumps 210 on the basis of the control data. The blood vessel training is performed while the output control unit 414 is operated to control the pumps 210.

Figure 8:
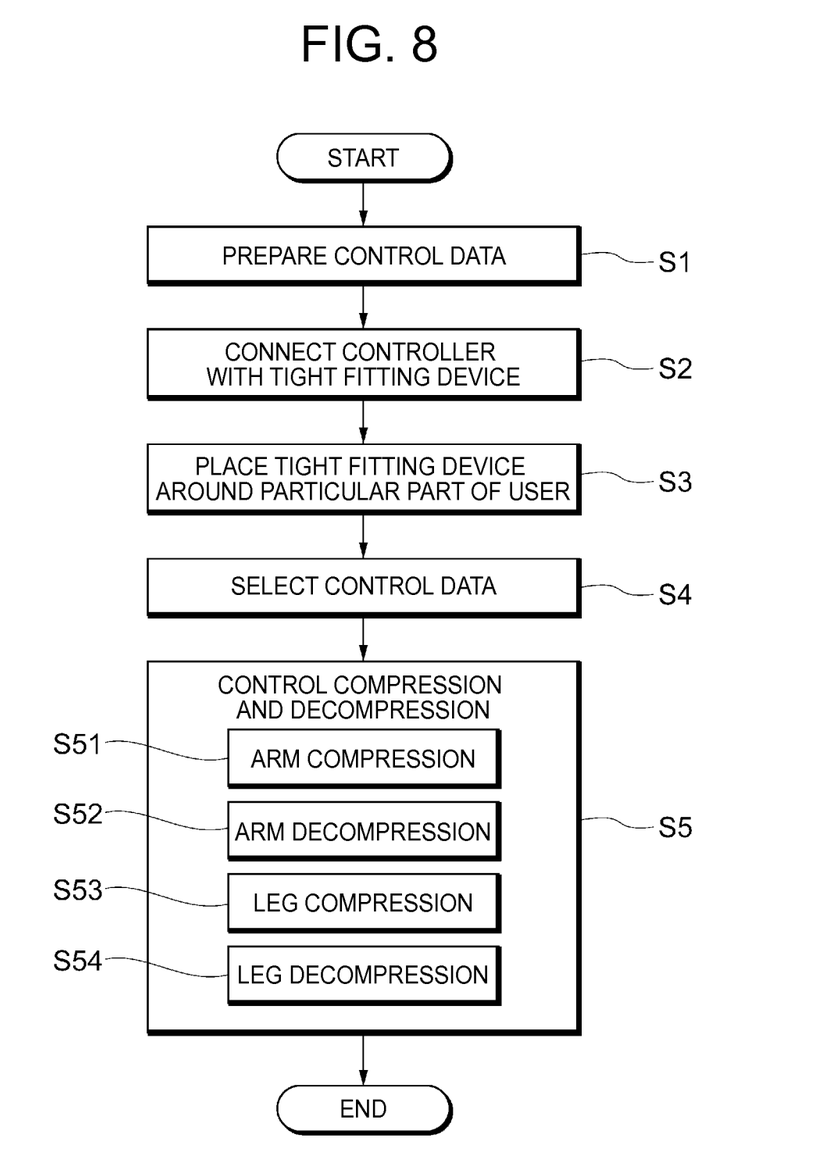
FIG. 8 is a flowchart for describing a method for strengthening blood vessels pertaining to an embodiment of the present invention.

Next, with reference to the flowchart in FIG. 8 and the like, the blood vessel training (method for strengthening blood vessels) performed by using the compression and decompression control system 1 pertaining to the present embodiment will be described.

First, control data for strengthening blood vessels is prepared (control data preparation step: S1). The compression and decompression controller 200 in the present embodiment is operated in two modes, a program mode and a training mode. The control data is prepared in the program mode. An input for selecting the program mode or the training mode is made with the input device. When information of selecting the program mode or the training mode is input from the input device, the input information analyzing unit 411 receives the information via the interface 404 and sends the information to the control unit 415. On receiving the information, the control unit 415 starts the program mode or the training mode.

When the program mode is active in the compression and decompression controller 200, the input device can be used to input information required to generate control data. The input information is sent to the control data generating unit 412 via the interface 404 and the input information analyzing unit 411. The control data generating unit 412 generates control data on the basis of the input information and sends the control data to the control data recording unit 413. The control data recording unit 413 stores the data. As described above, the control data in the present embodiment is composed of a set of four pieces of data associated with the respective four pumps 210. The control data is the data indicating how the pressure in the pump 210 is changed with time. How the pressure in the pump 210 is changed with time will be described later.

In the present embodiment, plural sets of four pieces of data can be stored in the control data recording unit 413, and thus the above input operation is repeated a required number of times. As described above, in the present embodiment, what is called a custom-made control data set suitable for each user receiving the blood vessel training is generated. Typical or general control data may be previously stored in the control data recording unit 413 before shipment of the compression and decompression controller 200. The number of pieces of the control data previously stored in the control data recording unit 413 is one or more.

After the preparation of the control data, the compression and decompression controller 200 is connected with the tight fitting devices 100 through the connection tubes 300 (device connection step: S2). Next, the tight fitting devices 100 are placed around particular parts of the limbs of a user as shown in FIG. 3 and FIG. 4 and are fastened to the particular parts with the shape retaining members 130 (tight fitting device placing step: S3). In this condition, substantially no compression force is applied to the particular parts. In the present embodiment, the particular parts are positions near the bases of both arms and positions near the bases of both legs.

In this condition, the compression and decompression controller 200 is switched to the training mode to perform the blood vessel training. After the start of the training mode, the user receiving the blood vessel training operates the input device to select the set of four pieces of control data for the user (control data selection step: S4). If having plural sets of the control data for the user, the user selects an appropriate control data set in consideration of physical conditions and other conditions of the user. The control data set is also selected with the input device.

When information of selecting a control data set is input from the input device, the information is sent to the control unit 415 via the interface 404 and the input information analyzing unit 411. The control unit 415 reads the control data set selected by the information out from the control data recording unit 413 and sends the control data set to the output control unit 414. The output control unit 414 controls the pumps 210 on the basis of the control data set (compression and decompression control step: S5). The pump 210 automatically keeps the pressure in the pump 210 at a value indicated by the control data while the pressure in the pump 210 is measured with a pressure gauge.

Here, a way to achieve the compression operation and the decompression operation in the compression and decompression control step S5 will be described with reference to the timing diagrams in FIG. 9 and FIG. 10. In the present embodiment, the compression force (appropriate pressure) to be applied to arms of a user receiving the blood vessel training is 150 to 160 mmHg, and the appropriate pressure for legs is 250 to 260 mmHg.

Figure 9:
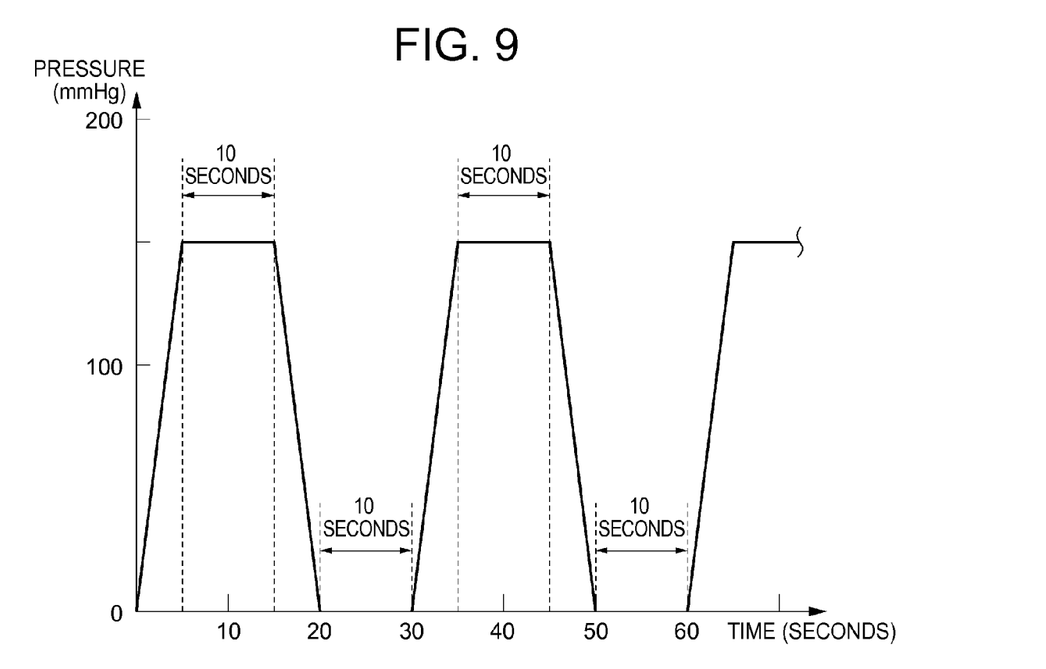
FIG. 9 is a timing diagram illustrating an exemplified time course of a compression force applied to a position near the base of an arm in the method for strengthening blood vessels pertaining to an embodiment of the present invention.

FIG. 9 is a timing diagram illustrating the time course of the compression force applied to a position near the base of an arm of a user with the band 110 of the tight fitting device 100. In the example shown in FIG. 9, the controller 220 controls the pump 210 to increase the compression force applied to the position near the base of the arm from 0 mmHg to an appropriate pressure (about 150 mmHg) over about 5 seconds and then to keep the appropriate pressure for about 10 seconds (arm compression step; S51). Next, the controller 220 controls the pump 210 to reduce the compression force applied to the position near the base of the arm from the appropriate pressure (about 150 mmHg) to 0 mmHg over about 5 seconds (or to completely remove the compression force) and then to keep the condition for about 10 seconds (arm decompression step: S52). Then, the controller 220 repeats the arm compression step S51 and the arm decompression step S52 twice or more (for example, each step is repeated three times).

Figure 10:
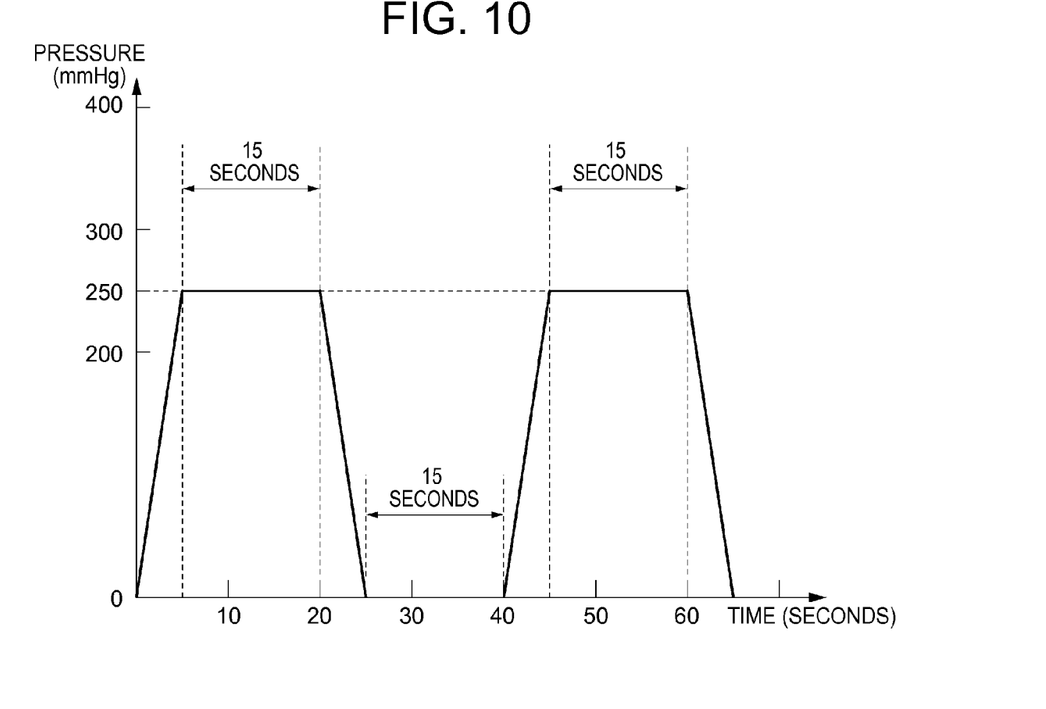
FIG. 10 is a timing diagram illustrating an exemplified time course of the compression force applied to a position near the base of a leg in the method for strengthening blood vessels pertaining to an embodiment of the present invention.

FIG. 10 is a timing diagram illustrating the time course of the compression force applied to a position near the base of a leg of a user with the band 110 of the tight fitting device 100. In the example shown in FIG. 10, the controller 220 controls the pump 210 to increase the compression force applied to the position near the base of the leg from 0 mmHg to an appropriate pressure (about 250 mmHg) over about 5 seconds and then to keep the appropriate pressure for about 15 seconds (leg compression step; S53). Next, the controller 220 controls the pump 210 to reduce the compression force applied to the position near the base of the leg from the appropriate pressure (about 250 mmHg) to 0 mmHg over about 5 seconds (or to completely remove the compression force) and then to keep the condition for about 15 seconds (leg decompression step: S54). Then, the controller 220 repeats the leg compression step S53 and the leg decompression step S54 twice or more (for example, each step is repeated five times).

In the compression and decompression control system 1 of the embodiment described above, the compression force applied with the band 110 can be controlled in such a manner that the compression operation applying predetermined compression forces to particular parts of the limbs (arms and legs) of a user and the decompression operation completely removing the compression forces applied to the particular parts by the compression operation are alternately repeated. This control allows the vascular endothelial cells of blood vessels of the user to generate a larger amount of nitric oxide, thereby strengthening the blood vessels. In other words, by simply using the particular bands 110 and repeating the compression and decompression of particular parts of the limbs of a user, blood vessels of the user can be extremely easily strengthened.

The compression and decompression control system 1 of the embodiment described above can control the compression force applied to the particular parts of the limbs of a user with the bands 110 in such a manner that the compression operation and the decompression operation are alternately repeated twice or more, and thus can stabilize autonomic nerves of the user. In other words, the compression operation can enhance the activity of sympathetic nerves of a user, whereas the decompression operation can enhance the activity of parasympathetic nerves of the user. The repetition of the compression operation and the decompression operation can thus stabilize autonomic nerves of the user.

The embodiments above have exemplified that each duration of the compression operation and the decompression operation is about 10 seconds for arms and is about 15 seconds for legs in the compression step and the decompression step of the blood vessel training. Each duration of the compression operation and the decompression operation is not limited to the above and can be appropriately changed in consideration of the physique, physical conditions at the time of the training, or other conditions of a user. Each duration of the compression operation and the decompression operation may be about 20 to 30 seconds, for example. The duration of the compression operation may differ from the duration of the decompression operation.

The embodiments above have exemplified that the compression forces applied in the compression step of the blood vessel training are set to the respective appropriate pressures (about 150 mmHg for arms and about 250 mmHg for legs). The compression force applied in the compression step of the blood vessel training is not limited to the above and can be appropriately changed in consideration of physical conditions at the time of training or other conditions of a user. For example, slightly lower compression forces (about 100 mmHg for arms and about 200 mmHg for legs) than the appropriate pressures can be applied, or slightly high compression forces (about 200 mmHg for arms and about 300 mmHg for legs) than the appropriate pressures can be applied.

The embodiments above have exemplified that the number of times of each of the compression step and the decompression step of the blood vessel training is three times for arms and five times for legs. The number of times of each of the compression step and the decompression step is not limited to the above and can be appropriately changed in consideration of the physique, physical conditions at the time of the training, or other conditions of a user. For example, the number of times of each of the compression step and the decompression step may be around ten times for both the arms and the legs.

The embodiments above have exemplified the blood vessel training (method for strengthening blood vessels) by using the compression and decompression control system 1 including the compression and decompression controller 200. The blood vessel training may be performed without such a compression and decompression control system 1. For example, an instructor places the bands 110 around the particular parts of the limbs of a user receiving the blood vessel training and applies predetermined compression forces to the particular parts (compression step), then keeps the compression step for a predetermined period of time, and completely removes the compression forces (decompression step). Alternate repetition of the compression step and the decompression step allows the vascular endothelial cells of blood vessels of the user receiving the training to generate a larger amount of nitric oxide, thereby strengthening the blood vessels.

EXAMPLE

Figure 11:
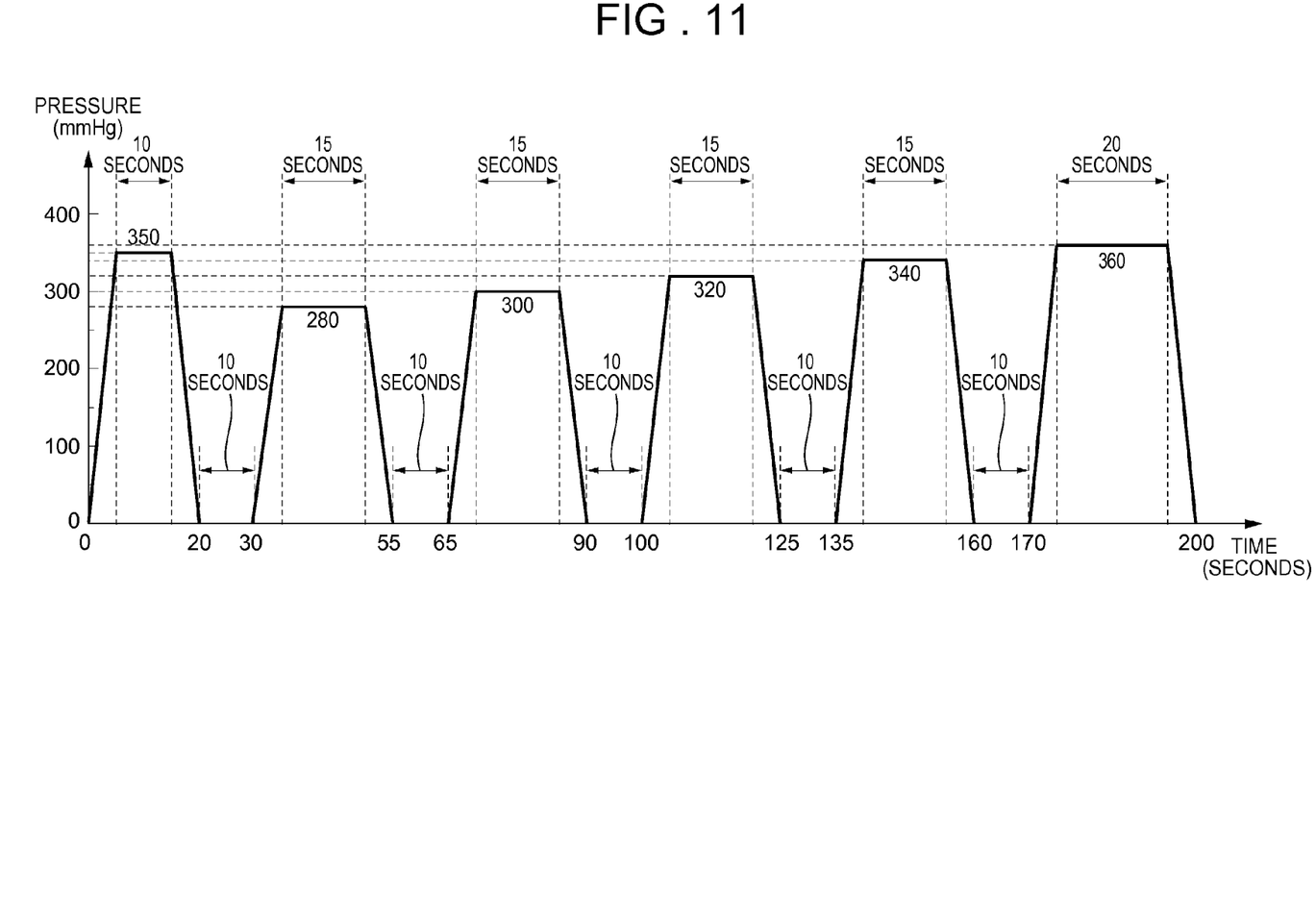
FIG. 11 is a timing diagram illustrating a time course of the compression force applied to a position near the base of an arm in the method for strengthening blood vessels pertaining to an example the present invention.

An Example of the present invention will next be described with reference to FIG. 11. In the example, a compression and decompression control system 1 similar to that described in the above embodiment was used. A user placed the band 110 around an arm of the user and performed the blood vessel training (method for strengthening blood vessels). The results obtained in the example will be described.

In the example, a tight fitting device 100A for arms including a band 110 (having a length of 90 cm and a width of 2.5 cm) made of neoprene rubber was used to perform the blood vessel training. The gas bag 120 (having a length of 25 cm and a width of 2.5 cm) used was a commercially available rubber bag, the shape retaining member 130 used was a commercially available hook and loop fastener, and the connection tube 300 used was a commercially available rubber tube. The compression and decompression controller 200 (pump 210 and controller 220) used was prepared by integrating a product (trade name: "KAATSU Master" (registered trademark)) manufactured by KAATSU JAPAN with a novel control program and control data for blood vessel training.

The compression and decompression control step of the blood vessel training in the example is configured by slightly modifying the compression and decompression manner in the compression and decompression control step S5 described in the above embodiment (other steps are the same as those in the above embodiment and thus are not described in detail). Specific operations for achieving compression and decompression will be described with reference to the timing diagram in FIG. 11. FIG. 11 is a timing diagram illustrating a time course of the compression force applied to a position near the base of an arm of a user with the band 110 of the tight fitting device 100A.

In the example, first, the controller 220 of the compression and decompression controller 200 controlled the pump 210 to increase the compression force applied to a position near the base of an arm of the user over about 5 seconds from 0 mmHg to a limit pressure (about 350 mmHg) at which the blood flow temporarily stopped and to keep the limit pressure for about 10 seconds (first compression step). In the first compression step, the user visually observed the conditions of the palm of the user and measured the pulse of the arm of the user, thereby identifying the hemostasis at the position near the base of the arm. Then, the controller 220 controlled the pump 210 to reduce the compression force applied to the position near the base of the arm of the user over about 5 seconds from the limit pressure (about 350 mmHg) to 0 mmHg (or to completely remove the compression force) and to keep the condition for about 10 seconds (first decompression step).

Next, the controller 220 controlled the pump 210 to increase the compression force applied to the position near the base of the arm of the user over about 5 seconds from 0 mmHg to about 280 mmHg and to keep the pressure for about 15 seconds (second compression step). Then, the controller 220 controlled the pump 210 to reduce the compression force applied to the position near the base of the arm of the user over about 5 seconds from about 280 mmHg to 0 mmHg (or to completely remove the compression force) and to keep the condition for about 10 seconds (second decompression step).

Next, the controller 220 controlled the pump 210 to increase the compression force applied to the position near the base of the arm of the user over about 5 seconds from 0 mmHg to about 300 mmHg and to keep the pressure for about 15 seconds (third compression step). Then, the controller 220 controlled the pump 210 to reduce the compression force applied to the position near the base of the arm of the user over about 5 seconds from about 300 mmHg to 0 mmHg (or to completely remove the compression force) and to keep the condition for about 10 seconds (third decompression step).

Next, the controller 220 controlled the pump 210 to increase the compression force applied to the position near the base of the arm of the user over about 5 seconds from 0 mmHg to about 320 mmHg and to keep the pressure for about 15 seconds (fourth compression step). Then, the controller 220 controlled the pump 210 to reduce the compression force applied to the position near the base of the arm of the user over about 5 seconds from about 320 mmHg to 0 mmHg (or to completely remove the compression force) and to keep the condition for about 10 seconds (fourth decompression step).

Next, the controller 220 controlled the pump 210 to increase the compression force applied to the position near the base of the arm of the user over about 5 seconds from 0 mmHg to about 340 mmHg and to keep the pressure for about 15 seconds (fifth compression step). Then, the controller 220 controlled the pump 210 to reduce the compression force applied to the position near the base of the arm of the user over about 5 seconds from about 340 mmHg to 0 mmHg (or to completely remove the compression force) and to keep the condition for about 10 seconds (fifth decompression step).

Subsequently, the controller 220 controlled the pump 210 to increase the compression force applied to the position near the base of the arm of the user over about 5 seconds from 0 mmHg to about 360 mmHg that was higher than the limit pressure of the user and to keep the pressure for about 20 seconds (sixth compression step). In the sixth compression step, the user visually observed the conditions of the palm of the user and measured the pulse of the arm of the user, thereby identifying no hemostasis at the position near the base of the arm. This result means that the sequence of the second, third, fourth, and fifth compression and decompression steps allowed the vascular endothelial cells of blood vessels of the user to generate a larger amount of nitric oxide, thus enhanced the vessel elasticity, and consequently increased the limit pressure (compression force causing hemostasis) of the user. Then, the controller 220 controlled the pump 210 to reduce the compression force applied to the position near the base of the arm of the user over about 5 seconds from about 360 mmHg to 0 mmHg, and the blood vessel training was completed.

The example above shows that the control of the compression force applied with the band 110 in such a manner that a compression operation applying a predetermined compression force to a position near the base of an arm of an user and a decompression operation completely removing the compression force to the position near the base of the arm by the compression operation are alternately repeated allows the vascular endothelial cells of blood vessels of the user to generate a larger amount of nitric oxide, thereby strengthening the blood vessels (enhancing the vessel elasticity).

The present invention is not limited to the embodiments above, and appropriate modifications made by a person skilled in the art are encompassed in the scope of the invention without departing from the features of the present invention. In other words, each element and the configurations, materials, conditions, shapes, sizes, and other features thereof included in the embodiments are not limited to the exemplified items and can be appropriately modified. The elements included in the embodiments can be combined in a technically feasible manner, and such a combination is encompassed in the scope of the invention without departing from the features of the present invention.

DESCRIPTION OF REFERENCE NUMERALS

1 compression and decompression control system
110 band
120 gas bag
130 shape retaining member
210 pump (pressure control unit)
220 controller
S51 arm compression step
S52 arm decompression step
S53 leg compression step
S54 leg decompression step

The invention claimed is:

1. A compression and decompression control system comprising:
   a band adapted to be placed around a particular part of a limb of a user and to apply a compression force to the particular part; and
   a controller for controlling the compression force applied to the particular part with the band,
   wherein the controller controls the compression force applied with the band in a manner that a compression operation applying a predetermined compression force to the particular part and a decompression operation completely removing the compression force applied to the particular part by the compression operation are alternately repeated, and
   wherein, for plural times of the compression operations, the controller sets the compression force in each compression operation to be higher than the corresponding compression force in the next preceding compression operation.

2. The compression and decompression control system according to claim 1, further comprising:
   a shape retaining member for retaining a loop shape of the band that has been placed around the particular part;
   a gas bag provided on the band; and
   a pressure control unit for supplying a gas to the gas bag through a certain tube or for removing a gas from the gas bag,
   wherein the controller controls the pressure control unit to achieve the compression operation and the decompression operation.

3. The compression and decompression control system according to claim 1, wherein the controller sets a duration of each of the compression operation and the decompression operation within a range from 10 to 30 seconds.

4. The compression and decompression control system according to claim 1, wherein the band has a width ranging from 2.5 to 3 cm and is placed around a position near a base of an arm of the user.

5. The compression and decompression control system according to claim 4, wherein the controller sets the compression force in the compression operation within a range from 100 to 200 mmHg.

6. The compression and decompression control system according to claim 4, wherein the controller sets the number of times of each of the compression operation and the decompression operation to three times.

7. The compression and decompression control system according to claim 4, wherein the controller sets the compression force in the compression operation within a range from 200 to 300 mmHg.

8. The compression and decompression control system according to claim 4, wherein the controller sets the number of times of each of the compression operation and the decompression operation to four or five times.

9. The compression and decompression control system according to claim 1, wherein the band has a width ranging from 5 to 6 cm and is placed around a position near a base of a leg of the user.

10. The compression and decompression control system according to claim 9, wherein the controller sets the compression force in the compression operation within a range from 200 to 300 mmHg.

11. The compression and decompression control system according to claim 9, wherein the controller sets the number of times of each of the compression operation and the decompression operation to five times.

12. A method for strengthening blood vessels, the method including no medical practice, the method comprising alternately repeating: a compression step of applying a compression force to a particular part of a limb of a user with a band that is adapted to be placed around the particular part; and a decompression step of completely removing the compression force applied to the particular part in the compression step, thereby allowing vascular endothelial cells of blood vessels of the user to generate a larger amount of nitric oxide to strengthen the blood vessels,
   wherein, for plural times of the compression steps, the compression force in each compression step is set to be higher than the corresponding compression force in the next preceding compression step.

13. The method for strengthening blood vessels according to claim 12, wherein a shape retaining member for retaining a loop shape of the band that has been placed around the particular part, a gas bag provided on the band, and a pressure control unit for supplying a gas to the gas bag through a certain tube or for removing a gas from the gas bag are used, and the pressure control unit is controlled to perform the compression step and the decompression step.

14. The method for strengthening blood vessels according to claim 12, wherein a duration of each of the compression step and the decompression step is set within a range from 10 to 30 seconds.

15. The method for strengthening blood vessels according to claim 12, wherein the band has a width ranging from 2.5 cm to 3 cm and is used to apply the compression force to a position near a base of an arm of the user in the compression step.

16. The method for strengthening blood vessels according to claim 15, wherein the compression force applied to the position near the base of the arm of the user is set within a range from 100 to 200 mmHg in the compression step.

17. The method for strengthening blood vessels according to claim 15, wherein the number of times of each of the compression step and the decompression step is set to three times.

18. The method for strengthening blood vessels according to claim 15, wherein the compression force applied to the position near the base of the arm of the user is set within a range from 200 to 300 mmHg in the compression step.

19. The method for strengthening blood vessels according to claim 15, wherein the number of times of each of the compression step and the decompression step is set to four or five times.

20. The method for strengthening blood vessels according to claim 12, wherein the band has a width ranging from 5 cm to 6 cm and is use to apply the compression force to a position near a base of a leg of the user in the compression step.

21. The method for strengthening blood vessels according to claim 20, wherein the compression force applied to the position near the base of the leg of the user is set within a range from 200 to 300 mmHg in the compression step.

22. The method for strengthening blood vessels according to claim 20, wherein the number of times of each of the compression step and the decompression step is set to five times.

23. A method for controlling a compression and decompression control system, the system including a band adapted to be placed around a particular part of a limb of a user and to apply a compression force to the particular part, the method comprising a compression and decompression control step of controlling the compression force applied with the band in a manner that a compression operation applying a predetermined compression force to the particular part and a decompression operation completely removing the compression force applied to the particular part by the compression operation are alternately repeated,
wherein, in the compression and decompression control step, for plural times of the compression operations, the compression force in each compression operation is set to be higher than the corresponding compression force in the next preceding compression operation.

24. The method for controlling a compression and decompression control system according to claim 23, wherein the compression and decompression control system further includes a shape retaining member for retaining a loop shape of the band that has been placed around the particular part, a gas bag provided on the band, and a pressure control unit for supplying a gas to the gas bag through a certain tube or for removing a gas from the gas bag, and in the compression and decompression control step, the pressure control unit is controlled to achieve the compression operation and the decompression operation.

25. The method for controlling a compression and decompression control system according to claim 23, wherein a duration of each of the compression operation and the decompression operation is set within a range from 10 to 30seconds in the compression and decompression control step.

26. The method for controlling a compression and decompression control system according to claim 23, wherein the band has a width ranging from 2.5 to 3 cm and is placed around a position near a base of an arm of the user, and in the compression and decompression control step, the compression force in the compression operation is set within a range from 100 to 200 mmHg.

27. The method for controlling a compression and decompression control system according to claim 26, wherein the number of times of each of the compression operation and the decompression operation is set to three times in the compression and decompression control step.

28. The method for controlling a compression and decompression control system according to claim 23, wherein the band has a width ranging from 2.5 to 3 cm and is placed around a position near a base of an arm of the user, and in the compression and decompression control step, the compression force in the compression operation is set within a range from 200 to 300 mmHg.

29. The method for controlling a compression and decompression control system according to claim 28, wherein the number of times of each of the compression operation and the decompression operation is set to four or five times in the compression and decompression control step.

30. The method for controlling a compression and decompression control system according to claim 23, wherein the band has a width ranging from 5 to 6 cm and is placed around a position near a base of a leg of the user, and in the compression and decompression control step, the compression force in the compression operation is set within a range from 200 to 300 mmHg.

31. The method for controlling a compression and decompression control system according to claim 30, wherein the number of times of each of the compression operation and the decompression operation is set to five times in the compression and decompression control step.

32. A compression and decompression control system comprising:
a band provided with a gas bag;
a fastener for retaining a loop shape of the band that has been placed around a particular part of at least any of limbs of a user;
a pump for supplying a gas to the gas bag through a certain tube or for removing a gas from the gas bag; and
a controller for controlling a compression force applied to the particular part with the band,
wherein the controller controls the pump in a manner that a compression operation applying a predetermined compression force to the particular part and a decompression operation completely removing the compression force applied to the particular part by the compression operation are alternately repeated, whereby controlling the compression force applied with the band, and
wherein, for plural times of the compression operations, the controller sets the compression force in each compression operation to be higher than the corresponding compression force in the next preceding compression operation.

\* \* \* \* \*